(12) United States Patent
Poueymirou et al.

(10) Patent No.: US 7,576,259 B2
(45) Date of Patent: *Aug. 18, 2009

(54) METHOD FOR MAKING GENETIC MODIFICATIONS

(75) Inventors: William Poueymirou, White Plains, NY (US); Thomas M. DeChiara, Katonah, NY (US); Wojtek Auerbach, Ridgewood, NJ (US); David Frendewey, New York, NY (US); David M. Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/904,559

(22) Filed: Sep. 27, 2007

(65) Prior Publication Data

US 2008/0028479 A1    Jan. 31, 2008

Related U.S. Application Data

(63) Continuation of application No. 11/254,045, filed on Oct. 19, 2005, now Pat. No. 7,294,754.

(60) Provisional application No. 60/619,999, filed on Oct. 19, 2004, provisional application No. 60/689,192, filed on Jun. 10, 2005.

(51) Int. Cl.
    *C12N 15/00* (2006.01)
(52) U.S. Cl. ............................................ 800/21; 800/25
(58) Field of Classification Search ................ 800/21, 800/25
    See application file for complete search history.

(56) References Cited

U.S. PATENT DOCUMENTS 6,485,972 B1    11/2002    McMahon et al.
7,294,754 B2 *  11/2007    Poueymirou et al. .......... 800/21

FOREIGN PATENT DOCUMENTS

WO    WO 2005/012511    2/2005

OTHER PUBLICATIONS

Adbelmassih et al. (2002) Laser-assisted ICSI: a novel approach to obtain higher oocyte survival and embryo quality . . . Human Reprod. 17/10:2694-2699.
Cotta-de-Almeida et al. (2003) A New Method for Rapidly Generating Gene-Targeting Vectors by Engineering BACs Through . . . Genome Res. 13:2190-2194.
Denning, C. et al. (2003) New frontiers in gene targeting and cloning: success, application and challenges in domestic . . . Reproduction 126:1-11.
Eggan et al. (2002) Male and female mice derived from the same embryonic stem celll clone by tetraploid embryo . . . Nature Biotech. 20:455-459.
Eggan et al. (2001) Hybrid vigor, fetal overgrowth, and viability of mice derived by nuclear cloning and tetraploid . . . PNAS 98/11:6209-6214.
Ogawa, K. et al. (2006) Synergistic action of Wnt and LIF in maintaining pluripotenoy of mouse ES cells. Biochem. Biophys. Res. Commun. 343:159-166.
Poueymirou et al. (2007) F0 generation mice fully derived from gene-targeted embryonic stem cells . . . Nature Biotech. 25:91-99.
Reya, T. et al. (2003) A role for Wnt signalling in self-renewal of haematopoietic stem cells. Nature 423:409-414.
Sato, N. et al. (2004) Maintenance of pluripotency in human and mouse embryonic stem cells through activation of Wnt . . . Nature Med. 10/1:55-63.
Shibamoto S. et al. (1998) Cytoskeletal reorganization by soluble Wnt-3a protein signalling. Genes to Cells 3:659-670.
Tokunaga et al. (1992) Effioacious Production of Viable Germ-Line Chimeras between Embryonic Stem (ES) . . . Develop. Growth & Differ. 34/5:561-566.
Yagi, A. et al. (1993) A Novel ES Cell Line, TT2, with High Germline-Differentiating Potency. Analytical Biochem. 214:70-76.
Zand et al. (2000) Interleukin-2 and Interferon-gamma Double Knockout Mice Reject Heterotopic Cardiac Allografts. Transplantation 70/9:1378-1381.
International Search Report for PCT/US2005/037584 (4 pages), Jan. 23, 2006.
International Preliminary Report on Patentability for PCT/US2005/037584 (7 pages), Apr. 24, 2007.
Dalton et al. (1993) Multiple Defects of Immune Cell Function in Mice with Disrupted Interferon-gamma Genes. Science 259:1739-1742.

* cited by examiner

*Primary Examiner*—Thaian N Ton
*Assistant Examiner*—Marcia S Noble
(74) *Attorney, Agent, or Firm*—Tor E. Smeland, Esq.; Ying-Zi Yang; Valeta Gregg, Esq.

(57) ABSTRACT

Methods of generating modified embryos and mammals by introduction of donor cells into an early stage embryo are provided, such that the resulting embryo and animal generated therefrom has a significant contribution to all tissues from the donor cells and is capable of transmitting the donor cell DNA.

18 Claims, No Drawings

METHOD FOR MAKING GENETIC MODIFICATIONS

CROSS-REFERENCE TO RELATED APPLICATIONS

This application is a continuation of U.S. patent application Ser. No. 11/254,045, filed 19 Oct. 2005, which claims the benefit under 35 USC § 119(e) of U.S. Provisional Patent Application No. 60/619,999 filed 19 Oct. 2004 and U.S. Provisional Patent Application No. 60/689,192 filed 10 Jun. 2005, which applications are herein specifically incorporated by reference in their entirety.

BACKGROUND

1. Field of the Invention

The invention is directed to improved methods for generating an animal homozygous for a genetic modification. More particularly, the present invention is directed to methods for increasing the efficiency of generating animals capable of transmitting a desired modification to subsequent offspring, for generating animals having high genetic material contribution from donor cells, and for increasing the efficiency of generating homozygous animals carrying the desired genetic modification.

2. Description of the Related Art

Methods for modifying eukaryotic donor cells are known in the art. See, for example, U.S. Pat. No. 6,586,251. Methods for generating transgenic animals are also known in the art. A proposed method for improving the efficiency of generating animals capable of transmitting a desired modification in TT2 ES cells is described in Yagi et al. (1993) Analytical Biochemistry 214:70-76.

BRIEF SUMMARY OF THE INVENTION

The invention is based in part on the realization that introduction of a modified cell into an early stage host embryo substantially increases the genetic material and cellular contribution of the donor cells to the host embryo, such that the animal produced has increased fraction of cells from the donor and thus has an increased likelihood of transmitting the modification through the germline. Further, the methods of the invention allow a broader range of donor cells to be used than was practical with prior art methods. The methods of the instant invention thus reduce the number of animals and breedings necessary to generate an animal homozygous for a modification.

In a first aspect, the invention features a method for generating a modified mammal, comprising: (a) introducing a eukaryotic donor cell into an early stage embryo; and (b) introducing the embryo of (a) into a surrogate mother for gestation, wherein a modified mammal is generated. The early stage embryo is a pre-morula stage cell. In a more specific embodiment, the early stage embryo is an 8-cell embryo. The early stage embryo may be derived from any strain. In one embodiment, an inbred embryo, e.g., C57BL/6, is used as host embryo. In another embodiment, an outbred embryo, e.g., Swiss Webster, is used as a host embryo.

The eukaryotic donor cell is a stem cell. More specifically, the stem cell is an embryonic stem (ES) cell or an ES-like cell. ES cells from any suitable ES cell line can be used in the method of the invention. In one embodiment, the ES cell is derived from an inbred strain, e.g., 129, C57BL/6, or BALB/c. In another embodiment, the ES cell is derived from a hybrid strain, e.g., C57BL/6×129. In a specific embodiment, the cell is a mouse ES cell. However, the method of the invention may be practiced with cells derived from other mammals, e.g., a rat ES or ES-like cell. In one embodiment, the ES or ES-like cell is a modified cell comprising a genetic modification. In a more specific embodiment, the modification may arise spontaneously, may be random, or may result from experimental manipulation, for example, by the introduction of a foreign nucleic acid. A foreign nucleic acid may be introduced by any method known to the art, e.g., by homologous recombination.

In a second aspect, the invention features a method for generating a mammal homozygous for a genetic modification, comprising: (a) introducing a female eukaryotic donor cell into an early stage host embryo, wherein the eukaryotic donor cell is heterozygous for the genetic modification; (b) maintaining the embryo of (a) in culture for further development; (c) introducing the embryo of (b) into a surrogate mother for gestation, wherein a modified female mammal is generated; (a') introducing a male eukaryotic donor cell into an early stage host embryo, wherein the eukaryotic donor cell is heterozygous for the genetic modification; (b') maintaining the embryo of (a') in culture for further development; (c') introducing the embryo of (b') into a surrogate mother for gestation, wherein a modified male mammal is generated; and (d) breeding the sexually mature female and male mammal of (c and c'), wherein a mammal homozygous for the genetic modification is generated.

In one embodiment, the female eukaryotic donor cell of step (a) is derived from the same cell line of the male eukaryotic donor cell of step (a'). In a more specific embodiment, the female eukaryotic donor cell of step (a) is an XO cell and the modified female mammal of step (c) is an XO mammal.

The male or female eukaryotic donor cell is a stem cell, preferably a heterozygous ES or ES-like cell. In one embodiment, the heterozygous ES cell is generated by (i) obtaining a large cloned genomic fragment containing a DNA sequence of interest; (ii) using bacterial homologous recombination to genetically modify the large cloned genomic fragment of (i) to create a large targeting vector for use in the eukaryotic donor cells (LTVEC, or large targeting vector); (iii) introducing the LTVEC of (ii) into the eukaryotic donor cells to modify an endogenous gene or chromosomal locus in the eukaryotic donor cells; and (iv) using a quantitative assay to detect modification of allele in the eukaryotic donor cells of (iii) to identify those eukaryotic donor cells in which the endogenous gene or chromosomal locus has been genetically modified.

In various embodiments, the culture conditions of step (b) and/or (b') allow the embryo to develop to a post-morula stage or further. In one embodiment, the culture conditions of step (b) and/or (b') are provided by a growth factor-conditioned culture medium. In a preferred embodiment, the growth factor is a protein of the Wnt family. In one embodiment, the Wnt protein is added to the culture medium directly. In another embodiment, the Wnt protein is produced by mouse L-cell. In yet another embodiment, the culture medium further comprises a leukemia inhibitor factor (LIF).

In one specific embodiment, a blastocyst stage embryo of (b) and/or (b') is introduced into a surrogate mother for gestation and further development.

The eukaryotic donor cell may be introduced into an early stage embryo by any method known to the art. In one embodiment, the eukaryotic donor cell is introduced under the zona pellucida of the early stage embryo. Other methodologies include removal of the zona pellucida membrane. In a more specific embodiment, the eukaryotic donor cell may be introduced under the zona pellucida by injection or other methods that create an opening in the zona pellucida. In one specific embodiment, an opening is created in the zona pellucida by a laser. In one embodiment, the laser comprises an infrared solid state diode laser. In another embodiment, the eukaryotic donor cell is introduced into the host embryo by cell fusion methods.

In one embodiment, a modified mammal comprising more than 90% donor cell-derived cells is bred in step (d). In a preferred embodiment, the modified mammal comprises more than 95% donor cell-derived cells. More preferably, the modified mammal comprises 100% donor cell-derived cells.

In a third aspect, the invention features a method of generating an embryo homozygous for a genetic modification, comprising: (a) introducing a female eukaryotic donor cell into an early stage host embryo, wherein the female eukaryotic donor cell is heterozygous for the genetic modification; (b) maintaining the embryo of (a) in culture for further development; (c) introducing the embryo of (b) into a surrogate mother for gestation, wherein a modified female mammal is generated; (a') introducing a male eukaryotic donor cell into an early stage host embryo, wherein the male eukaryotic donor cell is heterozygous for the genetic modification; (b') maintaining the embryo of (a') in culture for further development; (c') introducing the embryo of (b') into a surrogate mother for gestation, wherein a modified male mammal is generated; and (d) breeding the modified female and the modified male mammal of (c and c'), wherein an embryo homozygous for the genetic modification is generated.

In a fourth aspect, the invention features a method of generating a mammal homozygous for a genetic modification, comprising: (a) introducing a eukaryotic donor cell into an early stage embryo, wherein the eukaryotic donor cell is homozygous for the genetic modification; (b) maintaining the embryo of (a) in culture for further development; (c) introducing the embryo of (b) into a surrogate mother for gestation, wherein a mammal homozygous for the genetic modification is generated.

In one embodiment, the method for generating the eukaryotic donor cell homozygous for the genetic modification comprises a gene conversion, targeting both alleles of the same gene, or targeting either an X- or a Y-linked gene in a male ES cell.

In a fifth aspect, the invention features a method of generating an embryo homozygous for genetic modification, comprising: (a) introducing a eukaryotic donor cell into an early stage embryo, wherein the eukaryotic donor cell is homozygous for the genetic modification; and (b) culturing the early stage embryo of step (a), wherein an embryo homozygous for the genetic modification is generated.

In a sixth aspect, the invention features a method of increasing the relative contribution of genetic material from a donor eukaryotic donor cell to a host embryo, comprising: (a) introducing a eukaryotic donor cell into an early stage embryo; and (b) culturing the early stage embryo of step (a) under conditions that allow the embryo to develop to a post-morula stage or further.

In one embodiment, the culture conditions of step (b) allow the embryo to develop to a blastocyst. In another embodiment, the culture conditions of step (b) allow the embryo to develop to a gastrula or beyond. In various embodiments, the culture conditions of step (b) allow the embryo to develop to a post-morula stage or further. In one embodiment, the culture conditions of step (b) is provided by a growth factor-conditioned culture medium. In a preferred embodiment, the growth factor is a protein of the Wnt family. In one embodiment the Wnt protein is added to the culture medium directly. In another embodiment, the Wnt protein is produced by L-cells. In yet another embodiment, the culture medium further comprises a leukemia inhibitor factor (LIF).

In a seventh aspect, the invention features a method of generating a mammal having an increased relative contribution of genetic material from a donor eukaryotic donor cell to a host embryo, comprising: (a) introducing a eukaryotic donor cell into an early stage embryo; (b) culturing the early stage embryo of step (a) under conditions that allow the embryo to develop to a post-morula stage or further; and (c) introducing the embryo of (b) into a surrogate mother for gestation, wherein a mammal having an increased fraction of cells derived from the eukaryotic donor cell is generated.

In an eighth aspect, the invention features a method of generating a mammal capable of transmitting a genetic modification, comprising: (a) introducing a eukaryotic donor cell into an early stage embryo, wherein the eukaryotic donor cell carries a genetic modification; (b) culturing the early stage embryo of step (a) under conditions which allow the embryo to develop to a post-morula stage or further; and (c) introducing the embryo of (b) into a surrogate mother for gestation, wherein a mammal capable of transmitting the genetic modification is generated.

In a ninth aspect, the invention features a genetically modified mammal generated by a method of the invention. In a preferred embodiment, 90% or more of the cells of the mammal are donor cell-derived cells; more preferably, 95% or more of the cells of the mammal are donor cell-derived cells; even more preferably, 99% or more of the cells of the mammal are donor cell-derived cells. In one embodiment, 100% of the cells of the mammal are donor cell-derived cells.

In a tenth aspect, the invention features a genetically modified embryo generated by a method of the invention. In a preferred embodiment, 90% or more of the cells of the embryo are donor cell-derived cells; more preferably, 95% or more of the cells are donor cell-derived cells; even more preferably, 99% or more of the cells are donor cell-derived cells. In one embodiment, 100% of the cells of the embryo are donor cell-derived cells.

In an eleventh aspect, the invention features a culture medium for maintaining and/or growing an early stage embryo, wherein the culture medium comprises a growth factor.

In one embodiment, the growth factor is a protein of the Wnt family. The Wnt family protein is selected from the group consisting of Wnt1, Wnt3a, Wnt2, Wnt2b, Wnt3, Wnt4, Wnt5a, Wnt6, Wnt7a, Wnt8a, Wnt9a, Wnt9b, Wnt10a, Wnt10b, Wnt11, and Wnt16. In a preferred embodiment, the Wnt protein is Wnt3a. In one embodiment, the Wnt protein is a recombinant protein. In another embodiment, the culture medium is conditioned by a Wnt-producing mouse L-cell.

In one embodiment, the culture medium further comprises a maintenance agent. In one embodiment, the maintenance agent is a leukemia inhibitor factor (LIF)

Other objects and advantages will become apparent from a review of the ensuing detailed description.

DETAILED DESCRIPTION

Before the methods, constructs and transgenic animals of the present invention are described, it is to be understood that this invention is not limited to particular methods, constructs, transgenic animals, and experimental conditions described, as such all may vary. It is also to be understood that the terminology used herein is for the purpose of describing particular embodiments only, and is not intended to be limiting, since the scope of the present invention will be limited only by the appended claims.

As used in this specification and in the appended claims, the singular forms "a", "an" and "the" include plural references unless the context clearly dictates otherwise, e.g., "a cell" includes a plurality of cells. Thus, for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety.

Definitions

The term "embryonic stem (ES)-like cell" includes a cell that, upon introduction into an embryo, can contribute to any tissue of the developing embryo.

The terms "increased contribution", "higher relative percentage" and the like, include an improved genetic material contribution of a donor eukaryotic donor cell to an organism resulting from further development of a modified early stage host embryo. The method of the invention provides the means of increasing the probability that cells introduced into the host embryo contribute to all tissues, including germline tissues, of the generated animal.

By "gene knockout" as used herein is meant a genetic modification resulting from the disruption of the genetic information encoded at a chromosomal locus. By "gene knockin" as used herein is meant a genetic modification resulting from replacement of genetic information encoded at a chromosomal locus with a different DNA sequence or insertion of foreign genetic information at a chromosomal locus. By "knockout animal" as used herein is meant an animal in which a significant proportion of the animal's cells harbor a gene knockout. By "knockin animal" as used herein is meant an animal in which a significant proportion of the animal's cells harbor a genetic knockin.

General Description

One of the desired components of a transgenic animal study is generating a genetically modified transgenic animal capable of transmitting the genetic modification to progeny, i.e., a transgenic animal comprising the genetic modification in its germline. Current methods of creating such a transmission-capable transgenic animal tend to be inefficient in terms of resources and time expenditures. For example, to generate a genetically modified transgenic animal capable of transmitting the genetic modification to progeny, a modified ES cell heterozygous for a desired genetic modification is injected into a recipient blastocyst embryo, and the recipient embryo is implanted into a surrogate mother for gestation and birth of transgenic progeny. The resulting transgenic progeny are chimeric because some of the progeny's tissues are derived from the injected ES cells while other of the progeny's tissues are derived from the recipient embryo cells. Because of this chimerism, the injected ES cells comprising the genetic modification may or may not form germline tissues in the progeny and be capable of transmitting the genetic modification to the next generation. To determine whether a chimera is capable of transmitting the genetic modification, the chimera must be bred to another animal that does not carry the same genetic modification to establish if the desired modification is transmitted to the resulting progeny (F1). Detection of the desired genetic modification in the F1 progeny of the cross between the chimera and the other animal establishes that the chimera carries the desired genetic modification in its germline and is capable of transmitting the modification to its progeny (germline transmission). Typically, approximately 50% of chimeras exhibit germline transmission. Coat color is the most frequently used marker of the extent of ES cell contribution to the chimera and the transmission of ES cell genetic content to the F1 progeny.

The current need to generate an F1 generation to determine if the chimera is capable of transmitting the genetic modification is inefficient and costly in terms of time and the costs of breeding and maintaining F1 progeny. One method of improving the efficiency of the process for generating transgenic animals is provided by the instant invention, which allows introduction into pre-morula embryos of cells that generate animals having an increased genetic material contribution of the exogenous cells relative to the results obtained when donor cells are introduced into later stage embryos, e.g., blastocysts. As a result, a much higher percentage of the chimeras are germline transmitters. In some instances, about 100% of the chimeras are germline transmitters and thus these chimeras can transmit ES cell materials to their offspring.

Introducing donor cells into early stage host embryos, e.g., 8-cell embryos, provides several important benefits over the current methods, which teach the use of later stage host embryos, e.g., blastocysts. As shown in Example 1 below, the number of early stage embryos harvested from a donor mother (e.g., female BL/6 mouse) is higher than the number of later stage embryos harvested. Thus, fewer pregnant female mice are needed as donors, decreasing the cost of obtaining and maintaining pregnant female mice.

Further, as shown below, donor cells may be introduced into a smaller number of early stage host embryos than later stage embryos to generate the same number of chimeric animals, reducing the time and cost of introducing donor cells into embryos, e.g., when introduction is by microinjection, the amount of time spent on microinjections is greatly reduced.

The instant invention also allows culturing the donor cell-containing host embryo to post-morula stages, e.g., to a blastocyst stage or a gastrula stage, before being introduced into a surrogate mother for gestation. Since in vitro culturing conditions are more favorable for the donor cells than for the host embryo, the resulting embryo has a higher content of donor cell-derived cells compared to the method by which the morula stage host embryo is introduced into a surrogate mother for gestation.

An important improvement provided by the instant invention is that the number of animals generated that are capable of transmitting donor DNA is increased substantially with the use of early stage host embryos, such that an entire generation of breeding is eliminated. This is a significant practical improvement with important commercial implications.

A method known in the art that allows an entire generation of breeding to be eliminated employs tetraploid embryos as recipients of the modified donor cells. As the tetraploid cells of the recipient embryo are incapable of contributing to the tissue of the developing animal, the animals that are born are completely derived from the modified donor cells. If the resulting animals do not have a genetic modification that affects fertility, they will all be able to transmit the desired genetic modification to their progeny upon mating. This process is laborious and inefficient, producing only a small fraction of live birth from hybrid ES cell lines. Injections of cells under the zona pellucida of pre-morula stage diploid embryos produces increased survival and generation of larger number of completely or almost completely ES cell derived live animals. Both male and females can be obtained by this method.

The method of the invention can be applied to introduce inbred ES cells into outbred recipient embryos through microinjection.

Other features of the invention will become apparent in the course of the following descriptions of exemplary embodiments, which are given for illustration of the invention and are not intended to be limiting thereof.

EXAMPLES

The following examples are put forth so as to provide those of ordinary skill in the art with examples of how to make and use the methods, compositions and animals of the invention, and are not intended to limit the scope of the invention. Efforts have been made to ensure accuracy with respect to numbers used (e.g., amounts, temperature, etc.) but some experimental deviations are to be expected as is known to one of skill in the art. Unless indicated otherwise, parts are parts by weight, molecular weight is average molecular weight, temperature is in degrees Centigrade, and pressure is at or near atmospheric.

Example 1

Generation of Germline Transmitting Animals

Mouse embryos for injection were obtained from natural matings where the morning of the plug was designated as 0.5 days p.c. (post coitus). Oviducts were collected from plugged females at 2.5 days p.c. and were flushed with Dulbecco's medium to harvest the 8-cell embryos. The embryos were maintained in this medium for culture (37° C. in a 5% $CO_2$ incubator) and microinjection procedures.

The injection of the 8-cell embryos was performed using standard microinjection techniques except that prior to introduction of the ES cells, a hole was generated in the zona pellucida of the 8-cell embryo using an XY Clone laser system according to the manufacturer's specifications. The injection needle is inserted through this hole and 8 to 10 ES cells are deposited into the perivitelline space.

The injected embryos were transferred to a culture dish KSOM+AA and cultured overnight to the blastocyst stage. The surviving embryos were transferred as blastocysts to surrogate females in the afternoon of the next day (3.5 days p.c.).

Example 2

Generation of Homozygous DLL4 Knockout Mouse

Homozygous DLL4 knockout ES cells were microinjected into an 8-cell mouse embryo as described above. Injected embryos were cultured to blastocyst stage and were transferred to a surrogate female for gestation. All DLL4 knockout embryos died during gestation. The cause of death was identical to that observed for embryos produced by conventional breeding of heterozygous mice. Observation of the null DLL4 phenotype in the F0 generation avoided the two generations of breeding that would normally be required to generate Dll4 null mice.

Example 3

Generation of Highly and Fully ES Cell-Derived F0 Mice with Genetic Modifications Genetically modified male F1H4 ES cells were microinjected into either 8-cell or blastocyst stage C57BL/6 embryos. The microinjected blastocyst embryos were transferred to a surrogate female for gestation immediately after the injection. The microinjected 8-cell embryos were further cultured in KSOM+AA culture medium to blastocyst stage and were then transferred to a surrogate female for gestation. The percentages of ES cell contribution were estimated by the coat color of the male F0 mice. Results are summarized in Table 1. As shown, when genetically modified ES cells were microinjected into 8-cell embryos, all of the F0 mice are ES cell-derived. On the other hand, when genetically modified ES cells were microinjected into blastocyst stage embryos, none of the male F0 mice were fully ES cell-derived and only about half of the male F0 mice (2 out 4 and 4 out of 7 for 494B-F5 and 1218X-E2, respectively) have more than 90% ES-derived cells (*Percentages of ES cell contribution were estimated by the coat color of F0 mice).

TABLE 1

| | | No. of Pups | | | No. of Male F0 Mice with Various Percentage of ES Cell Contribution* | | | | |
|---|---|---|---|---|---|---|---|---|---|
| | Embryo | | | | | | | | |
| ES Cell Line | Stage | No. | Total | Male | <50% | 50% to 80% | 90% | >90% | 100% |
| 494B-F5 | 8-Cell | 33 | 11 | 11 | 0 | 0 | 0 | 0 | 11 |
| 494B-F5 | Blastocyst | 20 | 5 | 4 | 0 | 0 | 2 | 2 | 0 |
| 1218X-E2 | 8-Cell | 50 | 6 | 6 | 0 | 0 | 0 | 0 | 6 |
| 1218X-E2 | Blastocyst | 36 | 7 | 4 | 0 | 0 | 0 | 4 | 0 |

More ES cell lines were used to test the effect of the host embryo stage (8-cell vs. blastocyst) on the ES cell contribution in the resulting male F0 mice. Similar results were obtained and are summarized in Table 2 (*Percentages of ES cell contribution were estimated by the coat color of F0 mice).

TABLE 2

| ES Cell Line | Embryo Stage | No. of Pups | | No. of Male F0 Mice with Various Percentage of ES Cell Contribution* | | | | |
|---|---|---|---|---|---|---|---|---|
| | | No. | Total | Male | <50% | 50% to 80% | 90% | >90% | 100% |
| F1H4 Parental | 8-Cell | 120 | 34 | 30 | 3 | 0 | 0 | 0 | 27 |
| F1H4 Parental | Blastocyst | 125 | 24 | 20 | 5 | 1 | 2 | 12 | 0 |
| 609B-G2 | 8-Cell | 50 | 17 | 15 | 2 | 0 | 0 | 0 | 13 |
| 609B-G2 | Blastocyst | 50 | 21 | 16 | 1 | 0 | 1 | 14 | 0 |
| 698B-A8 | 8-Cell | 25 | 5 | 4 | 1 | 0 | 0 | 1 | 2 |
| 698B-A8 | Blastocyst | 25 | 9 | 6 | 3 | 3 | 0 | 0 | 0 |
| 639C-A9 | 8-Cell | 37 | 12 | 11 | 1 | 0 | 0 | 0 | 10 |
| 639C-A9 | Blastocyst | 25 | 7 | 7 | 0 | 0 | 0 | 7 | 0 |
| 619A-A1 | 8-Cell | 25 | 12 | 11 | 1 | 0 | 0 | 0 | 10 |
| 619A-A1 | Blastocyst | 25 | 7 | 6 | 0 | 0 | 0 | 6 | 0 |
| 576A-E11 | 8-Cell | 25 | 12 | 10 | 1 | 0 | 0 | 0 | 9 |
| 576A-E11 | Blastocyst | 25 | 21 | 16 | 2 | 1 | 1 | 12 | 0 |

Example 4

Generation of Highly and Fully ES Cell-Derived Female F0 Mice

Genetically modified XO ES cells (648B-H12 clone) were microinjected into either 8-cell or blastocyst stage C57BL/6 embryos. The microinjected blastocyst embryos were transferred to a surrogate female for gestation immediately after the injection. The microinjected 8-cell embryos were further cultured in KSOM+AA culture medium to blastocyst stage and were then transferred to a surrogate female for gestation. The percentages of ES cell contribution in the female F0 mice were estimated by their coat color. As shown in Table 3, when genetically modified XO ES cells were microinjected into 8-cell embryos, all of the chimeras were females. When genetically modified ES cells were microinjected into blastocyst stage embryos, only 7 out of a total of 16 for 648B-H12 and 11 out of 16 for 648C-H1 F0 mice were female (*Percentages of ES cell contribution were estimated by the coat color of F0 mice).

TABLE 3

| | SW Embryo | | No. of Pups | No. of Chimera | | No. of Female F0 mice with Various Percentage of ES Cell Contribution* | | |
|---|---|---|---|---|---|---|---|---|
| XO Clone | Stage | No. | Pups No. | Total | Female | <90% | >90% | 100% |
| 648B-H12 | 8-Cell | 50 | 13 | 13 | 13 | 0 | 0 | 13 |
| 648B-H12 | Blastocyst | 50 | 28 | 16 | 7 | 1 | 6 | 0 |
| 648C-H1 | 8-Cell | 50 | 6 | 6 | 6 | 0 | 0 | 6 |
| 648C-H1 | Blastocyst | 50 | 27 | 16 | 11 | 1 | 10 | 0 |

Example 5

Generation of Highly and Fully ES Cell-Derived F0 Mice Using Outbred and Inbred Host Embryos Unmodified male inbred (C57BL/6) or hybrid (F1H4) ES cells were microinjected into either 8-cell stage or blastocyst stage Swiss Webster (SW) embryos. The microinjected blastocyst embryos were transferred to a surrogate female for gestation immediately after the injection. The microinjected 8-cell embryos were further cultured in KSOM+AA culture medium to blastocyst stage and were then transferred to a surrogate female for gestation. Results are summarized in Table 4 (*Percentages of ES cell contribution were estimated by the coat color of F0 mice).

TABLE 4

| | SW Embryo | | No. of Pups | | No. of Male F0 Mice with Various Percentage of ES Cell Contribution* | | |
|---|---|---|---|---|---|---|---|
| ES Cells | Stage | No. | Total | Male | <90% | >90% | 100% |
| F1H4 | 8-Cell | 140 | 46 | 46 | 34 | 4 | 8 |
| F1H4 | Blastocyst | 50 | 11 | 11 | 11 | 0 | 0 |
| C57/BL6.2 | 8-Cell | 75 | 19 | 6 | 0 | 0 | 6 |
| C57/BL6.2 | Blastocyst | 10 | 7 | 6 | 6 | 0 | 0 |

Similar results were obtained when male inbred 129 (CJ7) and BALB/c ES cells were microinjected into either 8-cell or blastocyst stage inbred C56BL/6 host embryos. Results are summarized in Table 5 (*Percentages of ES cell contribution were estimated by the coat color of F0 mice).

TABLE 5

| | C56BL/6 Embryo | | No. of Pups | | No. of Male F0 Mice with Various Percentage of ES Cell Contribution* | | |
|---|---|---|---|---|---|---|---|
| ES Cells | Stage | No. | Total | Male | <90% | >90% | 100% |
| 129 (CJ7) | 8-Cell | 57 | 8 | 8 | 3 | 0 | 5 |
| 129 (CJ7) | Blastocyst | 50 | 18 | 14 | 4 | 10 | 0 |
| BALB/c | 8-Cell | 50 | 11 | 11 | 5 | 0 | 6 |
| BALB/c | Blastocyst | 57 | 8 | 1 | 1 | 0 | 0 |

TABLE 5-continued

| | C56BL/6 Embryo | No. of Pups | | | No. of Male F0 Mice with Various Percentage of ES Cell Contribution* | | |
|---|---|---|---|---|---|---|---|
| ES Cells | Stage | No. | Total | Male | <90% | >90% | 100% |

Example 6

Highly and Fully ES Cell-Derived F0 Mice are Germline Transmission Competent F1H4-derived male F0 mice having more than 90% cells derived from the ES cells (more than 90% ES cell contribution) were used to test germline transmission competency. Using male ES cells, sexually mature male F0 mice were bred with sexually mature females. The coat color of the offspring was used as a marker for the evaluation of germline transmission competency. Results are summarized on Table 6. When 8-cell stage embryos were used as host embryos, over 95% (51 out of 53) of the F0 males generated by 8-cell microinjection exhibited 100% germline transmission competency. When blastocyst stage embryos were used as host embryos, only about 64% (57 out of 89) of the F0 males exhibited 100% germline transmission competency. In addition, about 21% (19 out of 89) of the F0 males generated by blastocyst microinjection did not produce any offspring compared to less than 4% (2 out of 53) of the F0 males generated by 8-cell microinjection with no offspring (**Percentages of germline transmission competency were estimated by the coat color of the corresponding offspring).

TABLE 6

| Stage of Host Embryo | No. of Male F0 Bred | No. of Male F0 Shown Various Percentage of Germline Transmission Competency** | | | No. of Male F0 with No Offspring |
|---|---|---|---|---|---|
| | | 100% | Partial | Zero | |
| 8-Cell | 53 | 51 | 0 | 0 | 2 |
| Blastocyst | 89 | 57 | 9 | 4 | 19 |

Example 7

Effect of Post-Microinjection Culture Medium on the Quality of F0 Mice

Modified male C57BL/6 and F1H4 ES cells were microinjected into 8-cell stage Swiss Webster (SW) embryos. The microinjected embryos were cultured in different culture media to blastocyst stage and were then transferred to a surrogate female for gestation. Three different culture media were used: (1) KSOM, mouse embryo culture medium; (2) LIF, ES cell culture medium containing LIF; (3) Wnt3, Wnt3 conditioned ES cell culture medium. Results are summarized in Table 7. Wnt3 conditioned ES medium was produced as following: (i) mouse L-cells were plated into a T75 flask in medium made of high glucose DMEM, 10% FBS, and L-glutamine, and were incubated at 37° C., with 5% $CO_2$; (ii) when cell density reached 100% confluency, 10% of the cells were re-plated into another T75 flask; (iii) the culture medium was collected until cell density reached confluency again (about 3 days after re-plating); and finally, (iv) the collected culture medium was mixed with equal volume of ES cell culture medium without LIF but with serum replacement (*Percentages of ES cell contribution were estimated by the coat color of F0 mice).

TABLE 7

| ES Cells | Culture Medium | No. Embryo Transferred | No. of Pups | | No. of Male F0 Mice with Various Percentage of ES Cell Contribution* | |
|---|---|---|---|---|---|---|
| | | | Total | Male | <100% | 100% |
| F1H4 | KSOM | 140 | 55 | 45 | 37 | 8 |
| F1H4 | LIF | 40 | 8 | 8 | 3 | 5 |
| F1H4 | Wnt3 | 40 | 9 | 9 | 2 | 7 |
| C57BL/6.2 | KSOM | 75 | 16 | 16 | 10 | 6 |
| C57BL/6.2 | LIF | 38 | 10 | 10 | 5 | 5 |
| C57BL/6.2 | Wnt3 | 38 | 11 | 11 | 0 | 11 |

Similar results were obtained when male modified F1H4 cells were microinjected into 8-cell C57BL/6 ES embryos.

Example 8

Generation of Animals Homozygous for a Genetic Modification from Heterozygous ES cells Male ES cells heterozygous for a desired genetic modification are microinjected into an 8-cell mouse embryo as described in Example 1. Female ES cells derived from the same male ES cell line and heterozygous for the same genetic modification are microinjected into another 8-cell mouse embryo as described above. Both embryos are cultured to the blastocyst stage and are transferred to a surrogate female for gestation. The resulting germline transmitting male and female F0 mice are bred to obtain progeny homozygous for the desired genetic modification. Two pairs of mice were bred. A total of 39 pups were born and 9 of these pups were homozygous for the genetic modification.

We claim:
1. A method for making a mouse embryo homozygous for a genetic modification, comprising:
 (a) incorporating a female mouse ES donor cell into a first pre-morula diploid mouse host embryo, wherein the female mouse ES donor cell is heterozygous for the genetic modification and is from an inbred strain;
 (b) culturing the first embryo to the blastocyst stage;
 (c) gestating the embryo of (b) in a surrogate mother, wherein upon gestation a modified female mouse is obtained having at least 90% cellular contribution from the female mouse ES donor cell;
 (a') incorporating a male mouse ES donor cell into a second pre-morula diploid mouse host embryo, wherein the male mouse ES donor cell is heterozygous for the genetic modification and is from an inbred strain;
 (b') culturing the embryo of (a') to the blastocyst stage;
 (c') gestating the embryo of (b') in a surrogate mother, wherein upon gestation a modified male mouse is obtained having at least 90% cellular contribution from the male mouse ES donor cell; and,
 (d) breeding the modified female mouse of (c) with the modified male mouse of (c') to obtain a mouse embryo homozygous for the genetic modification.

2. The method of claim 1, wherein the first and the second pre-morula host embryos are 8-cell stage embryos.

3. The method of claim 1, wherein the first and the second pre-morula host embryos are from an inbred strain.

4. The method of claim 1, wherein the first and the second pre-morula host embryos are from an outbred strain.

5. The method of claim 1, wherein the first and the second pre-morula host embryos each comprise a zona pellucida, and the ES donor cell is incorporated through an opening in the zona pellucida.

6. The method of claim 5, wherein the opening is produced by a laser.

7. A method for making a mouse embryo heterozygous for a genetic modification, comprising:
   (a) incorporating a mouse ES donor cell into a pre-morula diploid mouse host embryo, wherein the mouse ES donor cell is heterozygous for the genetic modification and is from an inbred strain;
   (b) culturing the embryo to the blastocyst stage;
   (c) gestating the embryo of (b) in a surrogate mother, wherein upon gestation a modified mouse embryo is obtained having at least 90% cellular contribution from the mouse ES donor cell.

8. The method of claim 7, wherein the pre-morula host embryo is an 8-cell stage embryo.

9. The method of claim 7, wherein the pre-morula host embryo is from an inbred strain.

10. The method of claim 7, wherein the pre-morula host embryo is from an outbred strain.

11. The method of claim 7, wherein the pre-morula embryo comprises a zona pellucida, and the mouse ES donor cell is incorporated through an opening in the zona pellucida.

12. The method of claim 11, wherein the opening is produced by a laser.

13. A method for making a mouse heterozygous for a genetic modification, comprising:
   (a) incorporating a mouse ES donor cell into a pre-morula diploid mouse host embryo, wherein the mouse ES donor cell is heterozygous for the genetic modification and is from an inbred strain;
   (b) culturing the embryo to the blastocyst stage;
   (c) gestating the embryo of (b) in a surrogate mother, wherein upon gestation a modified mouse is obtained having at least 90% cellular contribution from the mouse ES donor cell.

14. The method of claim 13, wherein the pre-morula host embryo is an 8-cell stage embryo.

15. The method of claim 13, wherein the pre-morula host embryo is from an inbred strain.

16. The method of claim 13, wherein the pre-morula host embryo is from an outbred strain.

17. The method of claim 13, wherein the embryo comprises a zona pellucida, and the mouse ES donor cell is incorporated through an opening in the zona pellucida.

18. The method of claim 17, wherein the opening is produced by a laser.

* * * * *